US008528550B2

(12) United States Patent
Cuzyldo et al.

(10) Patent No.: US 8,528,550 B2
(45) Date of Patent: Sep. 10, 2013

(54) OUTLET DEVICE FOR CONTROLLING ANESTHETIC FLOW IN VAPORIZER

(75) Inventors: Michael Cuzyldo, Orchard Park, NY (US); Michael Ide, Amherst, NY (US)

(73) Assignee: Piramal Critical Care, Inc., Orchard Park, NY (US)

( * ) Notice: Subject to any disclaimer, the term of this patent is extended or adjusted under 35 U.S.C. 154(b) by 721 days.

(21) Appl. No.: 12/630,174

(22) Filed: Dec. 3, 2009

(65) Prior Publication Data

US 2010/0199989 A1    Aug. 12, 2010

Related U.S. Application Data

(60) Provisional application No. 61/120,361, filed on Dec. 5, 2008.

(51) Int. Cl.
*A61M 16/20* (2006.01)
*A61M 16/00* (2006.01)
*B65D 47/30* (2006.01)

(52) U.S. Cl.
USPC .................. 128/203.19; 128/203.12; 222/546

(58) Field of Classification Search
USPC .............. 128/203.12–203.14; 222/546, 548, 222/549; 141/18, 21, 346, 351–354, 363–366
See application file for complete search history.

(56) References Cited

U.S. PATENT DOCUMENTS

| | | | |
|---|---|---|---|
| 2,584,167 A | | 2/1952 | Sundholm |
| 2,597,775 A | * | 5/1952 | Brown .......................... 239/476 |
| 2,989,091 A | | 6/1961 | Lowenthal |
| 3,216,630 A | * | 11/1965 | Stull ............................. 222/499 |
| RE26,193 E | | 4/1967 | Lobat |
| 3,326,402 A | | 6/1967 | Randazzo |
| 3,720,352 A | | 3/1973 | Kozlowski |
| 3,744,526 A | * | 7/1973 | MacNiel ................... 137/599.18 |
| 4,421,297 A | | 12/1983 | Pongrass et al. |
| 4,509,554 A | | 4/1985 | Failla |
| 4,949,875 A | | 8/1990 | Kuo |
| 5,026,924 A | | 6/1991 | Cicco |
| 5,287,898 A | | 2/1994 | Falb et al. |

(Continued)

FOREIGN PATENT DOCUMENTS

RU      2329832      7/2008

OTHER PUBLICATIONS

International Search Report corresponding to International Application No. PCT/US2009/051397 dated Sep. 15, 2009.

(Continued)

*Primary Examiner* — Justine Yu
*Assistant Examiner* — Michael Tsai
(74) *Attorney, Agent, or Firm* — Tarolli, Sundhei Covell & Tummino

(57) ABSTRACT

An apparatus and system for transferring a liquid, such as a liquid anesthetic, from a reservoir to a machine while minimizing the release of the liquid to the surrounding environment. The apparatus can include a first component having a through-hole, and a second component having an aperture, a support member extending into the aperture having a protrusion configured to be capable of sealing the through-hole, wherein a fluid in the reservoir may exit the reservoir by way of the through-hole and the aperture, wherein twisting the first component and second component relative to each other causes the protrusion to seal or unseal the through-hole thereby allowing or preventing the flow of fluid. A portion of the exterior surface of the second component can have a polygonal shape.

27 Claims, 15 Drawing Sheets

(56) References Cited

U.S. PATENT DOCUMENTS

| | | |
|---|---|---|
| 5,381,836 A | 1/1995 | Braatz et al. |
| 5,427,145 A | 6/1995 | Grabenkort |
| 5,488,973 A | 2/1996 | Yamamuro |
| 5,505,236 A | 4/1996 | Grabenkort et al. |
| 5,609,276 A | 3/1997 | Greatbatch |
| 5,617,906 A | 4/1997 | Braatz et al. |
| 5,682,874 A | 11/1997 | Grabenkort et al. |
| 5,687,777 A | 11/1997 | Dobson et al. |
| 5,915,427 A | 6/1999 | Grabenkort |
| 6,135,329 A | 10/2000 | Stoneberg et al. |
| 6,286,505 B1 | 9/2001 | Psaros |
| 6,296,623 B2 | 10/2001 | Spinello |
| 6,582,415 B1 | 6/2003 | Fowles et al. |
| 6,585,016 B1 | 7/2003 | Falligant et al. |
| 6,758,376 B1 | 7/2004 | Clodfelter et al. |
| 6,800,786 B1 | 10/2004 | Rozov et al. |
| 6,817,390 B2 * | 11/2004 | Falligant et al. ............ 141/352 |
| 7,159,616 B2 | 1/2007 | Watson et al. |
| 7,546,856 B2 | 6/2009 | Chotenovsky |
| 2006/0130930 A1 | 6/2006 | Turker et al. |
| 2007/0066955 A1 | 3/2007 | Sparholt et al. |
| 2007/0131725 A1 | 6/2007 | Friedman |
| 2007/0199616 A1 | 8/2007 | Chotenovsky |
| 2007/0204931 A1 | 9/2007 | Freed et al. |
| 2007/0204932 A1 | 9/2007 | Freed et al. |
| 2008/0302836 A1 | 12/2008 | Mathis |
| 2009/0260627 A1 | 10/2009 | Cuzydlo et al. |
| 2010/0018528 A1 | 1/2010 | Cuzydlo |
| 2010/0018607 A1 | 1/2010 | Cuzydlo |
| 2010/0108184 A1 | 5/2010 | Cuzydlo |
| 2010/0199987 A1 | 8/2010 | Cuzyldo |
| 2010/0199988 A1 | 8/2010 | Cuzyldo et al. |
| 2010/0199990 A1 | 8/2010 | Cuzyldo |
| 2010/0224285 A1 | 9/2010 | Cuzydlo |
| 2010/0319690 A1 | 12/2010 | Cuzydlo |

OTHER PUBLICATIONS

International Search Report corresponding to International Application No. PCT/US2009/051391 dated Sep. 17, 2009.
International Search Report corresponding to International Application No. PCT/US2009/62465 dated Jan. 14, 2010.
International Search Report corresponding to International Application No. PCT/US2009/62461 dated Feb. 12, 2010.
International Search Report corresponding to International Application No. PCT/US2009/066535 dated Mar. 12, 2010.
International Search Report corresponding to International Application No. PCT/US2010/026317 dated May 19, 2010.
International Search Report corresponding to International Application No. PCT/US2010/038179 dated Aug. 11, 2010.
International Preliminary Report on Patentability corresponding to International Application No. PCT/US2009/051391 dated Feb. 3, 2011.
International Preliminary Report on Patentability corresponding to International Application No. PCT/US2009/051397 dated Feb. 3, 2011.
Search Report TR 10/066 established by Russian Patent Office corresponding to Turkish Application No. 2009/08207 dated Aug. 9, 2010.
Search Report TR 09/591 established by Russian Patent Office corresponding to Turkish Application No. 2009/07308 dated Jun. 10, 2010.
Search Report TR 10/041 established by Russian Patent Office corresponding to Turkish Application No. 2009/00676 dated Aug. 9, 2010.
Search Report TR 10/130 established by Russian Patent Office corresponding to Turkish Application No. 2009/09123 dated Sep. 14, 2010.
Examination Report TR 08/349 corresponding to Turkish Application No. 2007/03378 dated Jan. 19, 2009.
Examination Report TR 09/551 corresponding to Turkish Application No. 2007/03378 dated May 10, 2010.
Office Action Dated Jun. 22, 2012 in U.S. Appl. No. 12/496,895.
Office Action Dated Mar. 7, 2012 in U.S. Appl. No. 12/274,819.
Office Action Dated Sep. 26, 2011 in U.S. Appl. No. 12/274,819.
International Search Report corresponding to International Application No. PCT/US09/62460.
Office Action Dated Apr. 27, 2012 in U.S. Appl. No. 12/608,081.
Office Action Dated May 16, 2012 in U.S. Appl. No. 12/608,092.
Office Action Dated May 23, 2012 in U.S. Appl. No. 12/630,174.
Office Action Dated May 23, 2012 in U.S. Appl. No. 12/631,936.
International Search Report corresponding to International Application No. PCT/US09/66920.
Office Action Dated Oct. 11, 2012 in U.S. Appl. No. 12/608,092.

* cited by examiner

OUTLET DEVICE FOR CONTROLLING ANESTHETIC FLOW IN VAPORIZER

CROSS-REFERENCE TO RELATED APPLICATION

This application claims the benefit under 35 U.S.C. §119 (e) of the earlier filing date of U.S. Provisional Application Ser. No. 61/120,361 filed on Dec. 5, 2008, the contents of which are hereby incorporated by reference.

FIELD OF INVENTION

This application discloses an invention which is related, generally and in various embodiments, to a device for supplying a liquid to a machine, such as a vaporizer.

BACKGROUND OF THE INVENTION

Liquid anesthetics are often packaged in glass bottles and shipped to a location where they may be used to anesthetize a patient undergoing a medical or dental procedure. Such anesthetics may also be used to induce analgesia in a patient undergoing a medical or dental procedure. In order to administer the anesthetic, the contents of the glass bottle are placed in a vaporizer. The vaporizer can vaporize the anesthetic and provide the vaporized anesthetic in a desired amount to the patient.

Inhalable anesthetics are typically volatile substances with relatively low boiling points and high vapor pressure. Preferably, there is little or no release of anesthetic to the atmosphere during handing. To bottle containing the vaporizer must be opened. Since it is unwise to expose medical personnel performing a procedure to an anesthetic, and since anesthetics are expensive, devices have been developed to minimize the release of anesthetic from a bottle to the environment surrounding a vaporizer. These devices, however, have failed to effectively minimize the release of anesthetic.

SUMMARY OF THE INVENTION

This application discloses an apparatus and system for transferring a liquid, such as an anesthetic, from a reservoir to a machine while effectively minimizing the release of the liquid to the surrounding environment. The apparatus can include a first component having a through-hole, and a second component having an aperture, a support member extending into the aperture having a protrusion configured to be capable of sealing the through-hole, wherein a fluid in the reservoir may exit the reservoir by way of the through-hole and the aperture, wherein twisting the first component and second component relative to each other causes the protrusion to seal or unseal the through-hole thereby allowing or preventing the flow of fluid. A portion of the exterior surface of the second component can have a polygonal shape.

DETAILED DESCRIPTION OF THE INVENTION

The accompanying drawings are intended to provide further understanding of the invention and are incorporated in and constitute a part of the description of the invention. The drawings illustrate an embodiment of the invention and together with the description illustrate principles of the invention.

The drawings should not be taken as implying any necessary limitation on the essential scope of invention. The drawings are given by way of non-limitative example to explain the nature of the invention.

For a more complete understanding of the instant invention reference is now made to the following description taken in conjunction with accompanying drawings.

The various features of novelty which characterize the invention are pointed out specifically in the claims which are a part of this description. For a better understanding of the invention, reference should be made to the drawings and descriptive matter in which there are illustrated and described preferred embodiments of invention.

Figure 1:
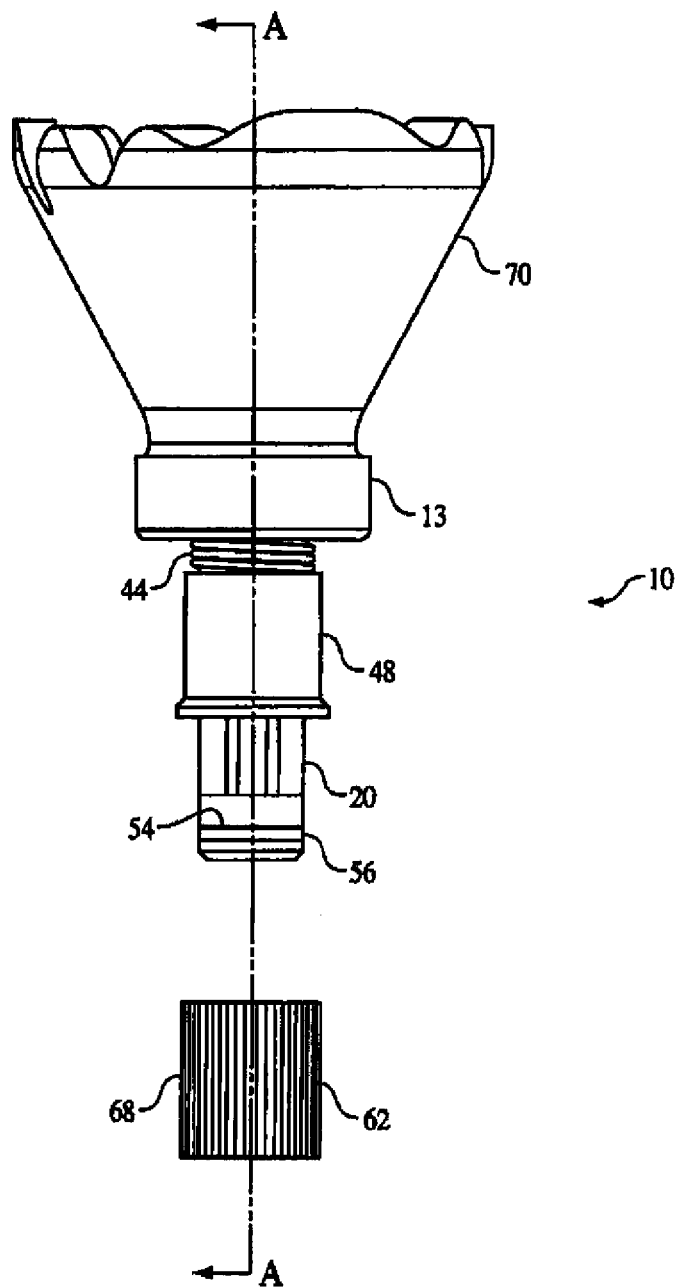
FIG. 1 illustrates a device according to the invention connected to an anesthetic agent bottle.
Figure 2:
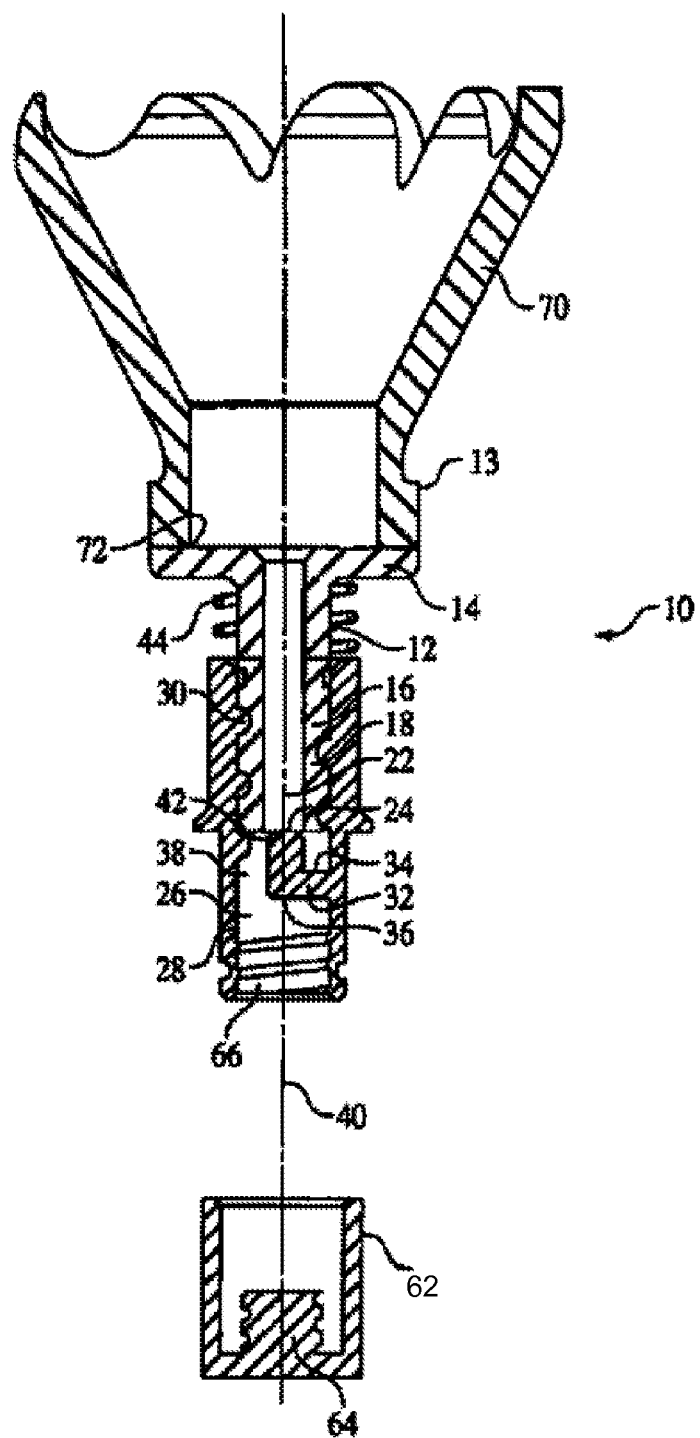
FIG. 2 illustrates a cross-section the device shown in FIG. 1 taken along A-A.
Figure 3A:
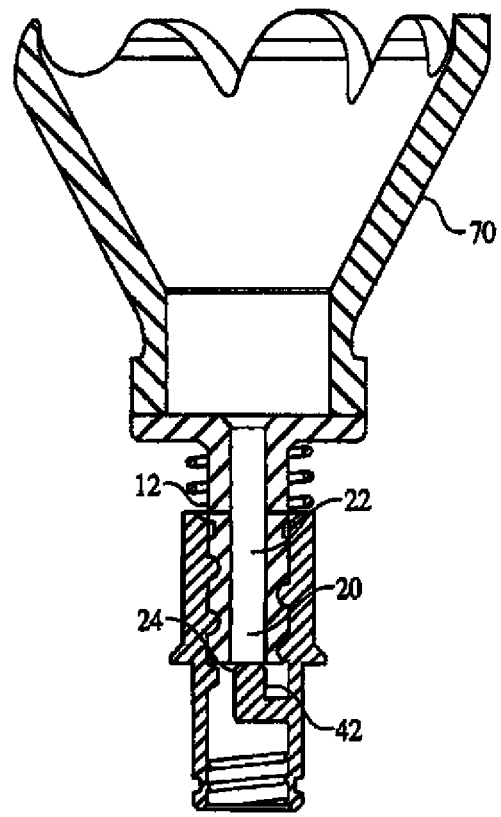
FIG. 3A illustrates a cross-section (along A-A) of the device shown in FIGS. 1 and 2 showing the device in an "open" position.
Figure 3A:
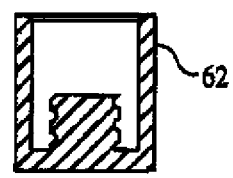
Figure 3B:
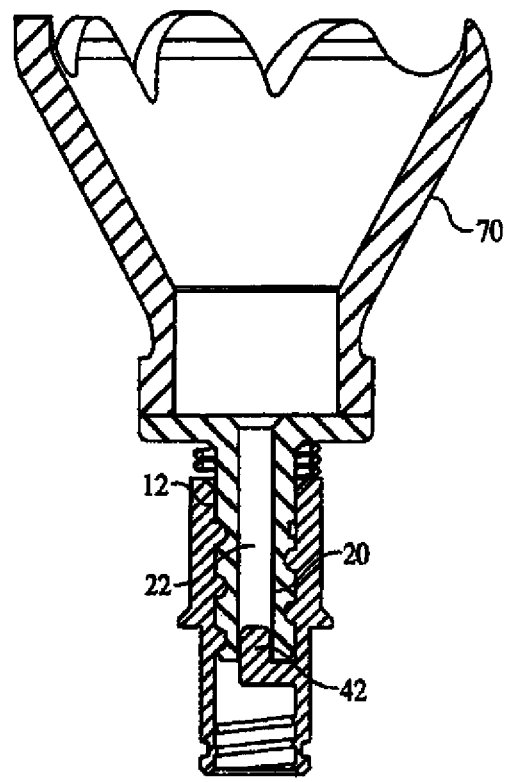
FIG. 3B illustrates a cross-section (along A-A) of the device shown in FIGS. 1 and 2 showing the device in the "closed" position.
Figure 3B:
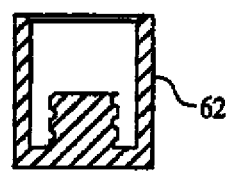

Referring now to the drawings, wherein like numerals designate identical or corresponding parts throughout the referred views, FIG. 1 shows an embodiment of an apparatus or device 10 for selectively opening or closing an anesthetic reservoir 70 which may hold a liquid such as a volatile anesthetic. Reservoir 70 can be a glass bottle or any other container capable of containing a liquid. Such a device 10 may include a first component 12 adaptable to the reservoir 70 and a second component 20 adaptable to a machine, for example, a vaporizer. The first component 12 may have a base 14 and a nozzle 16. The first component 12 may be attached to the reservoir 70 so that the base 14 may be in a sealing relation with an opening 72 of the reservoir 70. The base 14 may be attached to the reservoir using, for example, a clamping ring 13. The nozzle 16 may have an externally threaded portion 18. A through-hole 22 may extend through the base 14 and the nozzle 16. In this manner, a liquid contained within the reservoir 70 may flow from the reservoir 70 through the through-hole 22 and exit an orifice 24 in the first component 12. For example, it may be desired to transfer anesthetic from the reservoir 70 to a machine, such as a vaporizer, which dispenses the anesthetic to a person undergoing a medical procedure.

The second component 20 may have an aperture 26 defined by an inner surface 28. The inner surface 28 may have an internally threaded portion 30 to receive the externally threaded portion 18 of the nozzle 16. A support member 32 may extend into the aperture 26 from the inner surface 28. The support member 32 may occlude a portion of the aperture 26 but does not divide the aperture 26. In this manner, there may be a single passageway 38 leading from a first side 34 of the support member 32 to a second side 36 of the support member 32. The support member 32 may be oriented such that a primary plane 57 of the support member 32 is substantially transverse to the aperture 26 (see, e.g., FIGS. 4A and 4B). In an alternative embodiment, the support member 32 may be oriented such that a primary plane 59 of the support member 32 is substantially parallel to an axis 40 of the aperture 26 (see, e.g., FIGS. 5A and 5B).

A protrusion or knob 42 may extend from support member 32 toward the internally threaded portion 30. In this manner, by twisting the first component 12 and second component 20 relative to each other, the externally and internally threaded portions 18, 30 may cause the knob 42 to move toward or away from the orifice 24, depending on the direction in which twisting occurs. The knob 42 may be caused to be inserted in the orifice 24 and seated against the nozzle 16 thereby preventing liquid, which may be contained in the reservoir 70, from traveling from the reservoir 70 through the orifice 24 via the through-hole 22.

In operation, a single path is provided for liquid to travel from the reservoir 70, through the through-hole 22 of the first component 12, and through the aperture 26 of the second component 20. Similarly, vapor may travel in the opposite direction to the reservoir 70 along the same path. Because only a single path is provided, liquid will not travel from the reservoir 70 along this path at the same time that vapor is traveling into the reservoir 70, and vice versa. Instead, only liquid or only vapor will be contained in the path at any given time, thereby creating a gurgling effect as the alternate movement of liquid out and then vapor in occurs.

A biasing member or torsion spring 44 may be attached to the first component 12 and the second component 20 in order to provide a spring force to bias the first component 12 and the second component 20 to a predetermined position relative to each other. The torsion spring 44 may bias the device 10 to a "closed" position wherein the knob 42 is seated in the orifice 24 and against the nozzle 16 as described above. In this manner, anesthetic in the reservoir 70 can not escape unless a force is applied to the second component 20 to counter the force imposed by the torsion spring 44.

The exterior surface 46 of the second component 20 may have a first portion 48 adapted for extending from a vaporizer, and a second portion 50 adapted for insertion into a vaporizer. The first portion 48 may be a smooth cylindrical shape in which a circumference of a cross-section transverse to axis 40 may have a rounded shape with no flat sides (see, e.g., FIG. 5C). Alternatively, the first portion 48 may be a polygonal shape with three or more flat sides in combination with three or more rounded edges. The first portion 48 may be adapted for engaging a vaporizer.

Figure 4C:
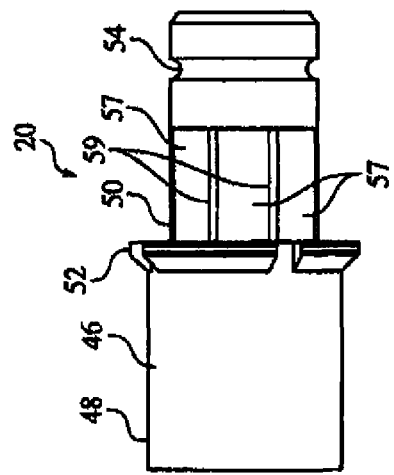
FIG. 4C is a side view of the second component shown in FIGS. 4A and 4B.
Figure 4A:
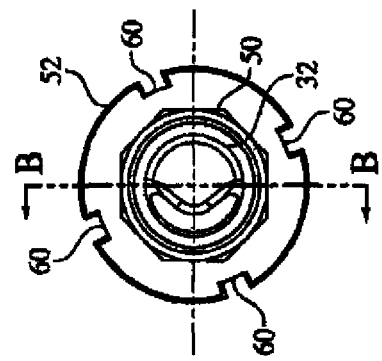
FIG. 4A illustrates an embodiment of the second component of a device according to the invention as viewed along the aperture.
Figure 4B:
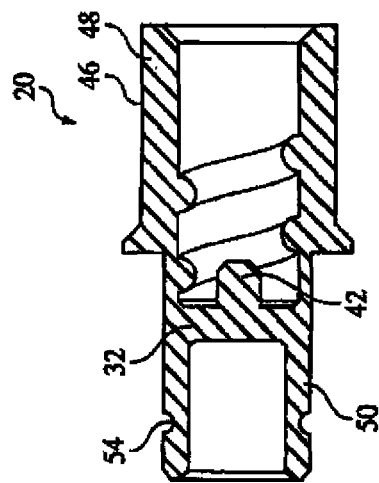
FIG. 4B is a cross-sectional view of the second component shown in FIG. 4A taken along B-B in FIG. 4A.
Figure 5C:
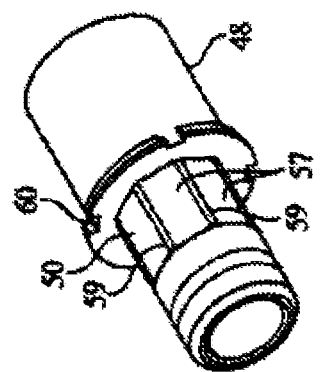
FIG. 5C is a perspective view of the second component shown in FIGS. 5A and 5B.
Figure 5A:
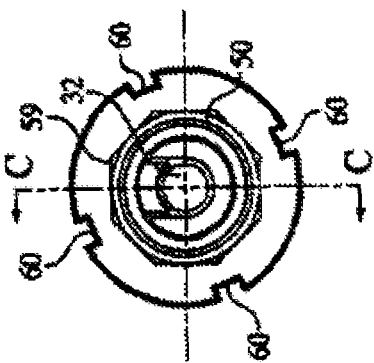
FIG. 5A illustrates another embodiment of the second component of a device according to the invention as viewed along the aperture.
Figure 5B:
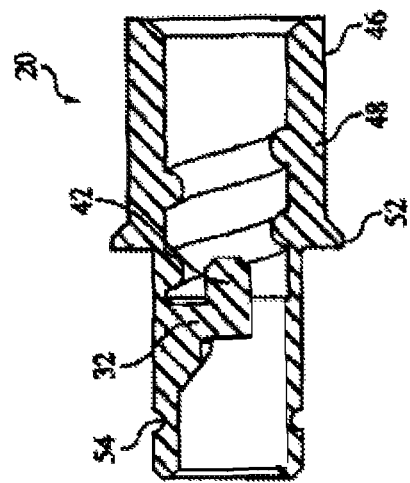
FIG. 5B is a cross-sectional view of the second component shown in FIG. 5A taken along C-C in FIG. 5A.

A part of the second portion 50 may be a polygonal shape with three or more flat sides 57 in combination with three or more rounded edges 59 (see, e.g., FIGS. 4C and 5C). The second portion 50 may have a groove 54 into which an O-ring 56 may be inserted to ensure a fluid-tight seal when connected to a vaporizer.

A transitional flange 52 may be provided to engage with a locking or holding device which may be located on a vaporizer. By engaging a vaporizer with the first portion 48, the transitional flange 52, or some combination of these, the device may be changed from a closed position to an open position while mounted to the vaporizer by rotating the reservoir 70.

Figure 6A:
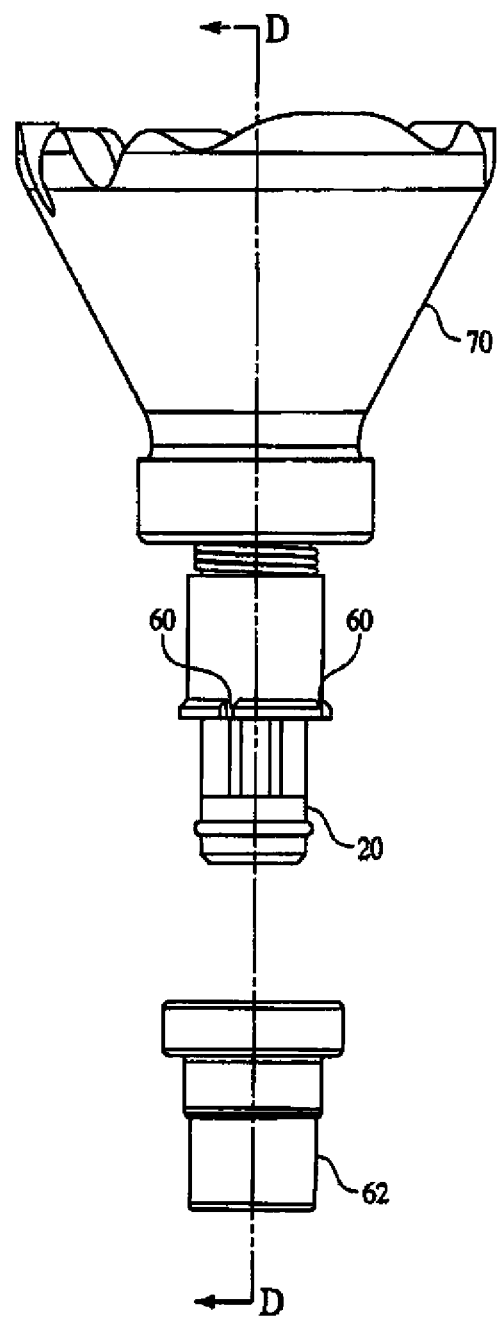
FIG. 6A is a side view of the device of FIG. 1 with a different cap.
Figure 6B:
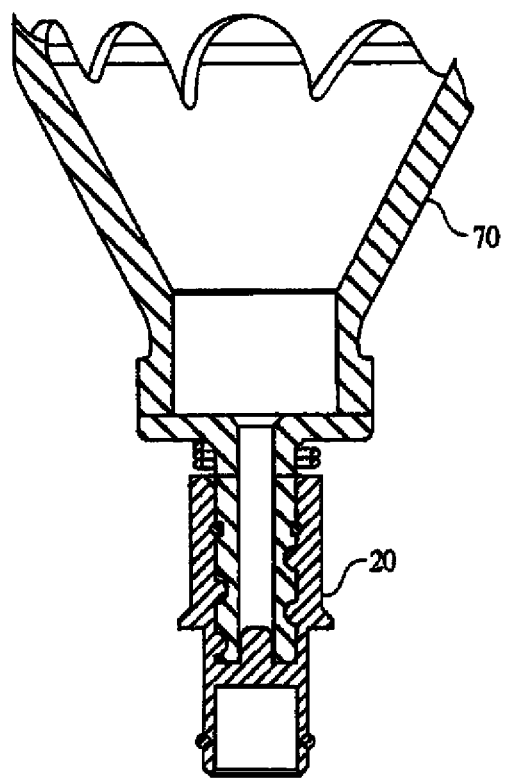
FIG. 6B is a cross-sectional view of the device shown in FIG. 6A taken along D-D.
Figure 6B:
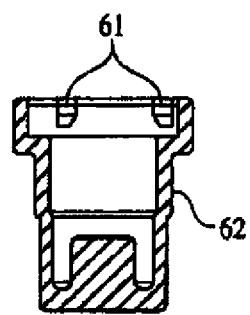

A cap 62 may be provided for covering the device 10 when not in use in a vaporizer. The cap 62 may have an externally threaded plug 64 which may engage with an internally-threaded outlet 66 of the second component 20 to secure the cap 62 to the device 10. The exterior surface 68 of the cap 62 may be knurled for improved grip. In another embodiment, the cap 62 may have tabs 61 for engaging notches 60 which may be in the transitional flange 52 (see, e.g., FIGS. 6A and 6B).

The support member 34 of the second component 20 may have a downstream side 35 adapted for pushing a plunger 83 which may reside in a receiving port 82 of a vaporizer. The plunger 83 may be a component of a valve in the vaporizer which allows anesthetic liquid provided by the reservoir 70 through device 10 to enter the vaporizer. The downstream side 35 of the support member 34 may be, for example, substantially flat such that a force applied to the plunger 83 by the support member 34 is directed substantially along a longitudinal dimension of the plunger 83.

Figure 7A:
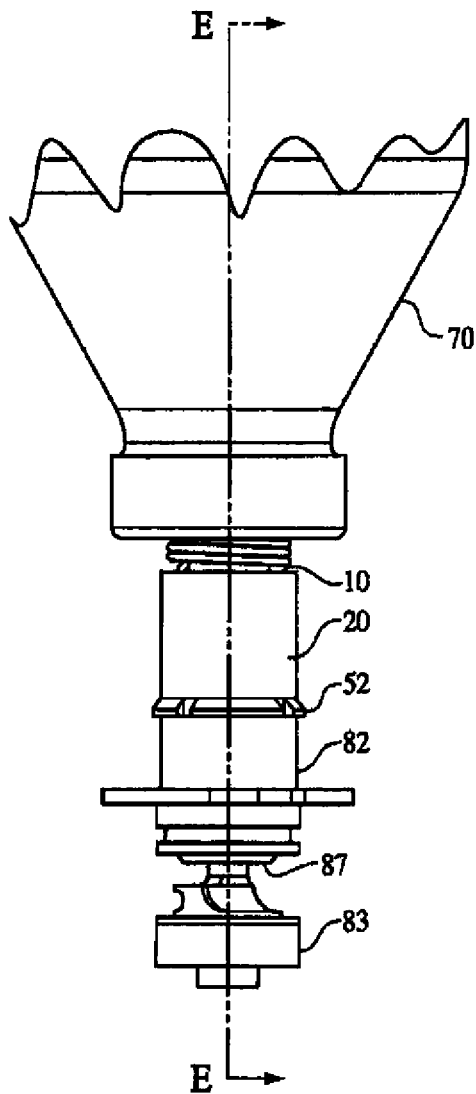
FIG. 7A is a side view of the device of FIG. 6A without a cap, but with the reservoir and a receiving port of a vaporizer, wherein the device is in a closed position and the receiving port is in an open position.
Figure 7B:
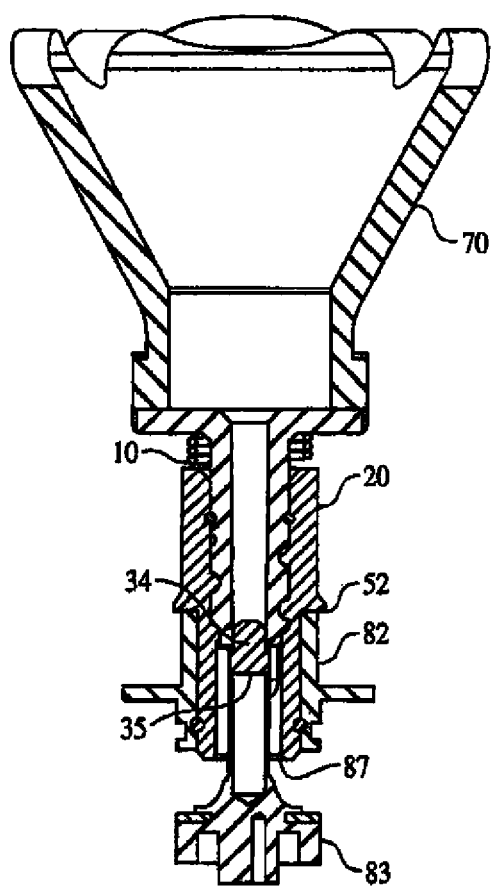
FIG. 7B is a cross-sectional view of the device, reservoir, and receiving port shown in FIG. 7A taken along E-E.
Figure 8A:
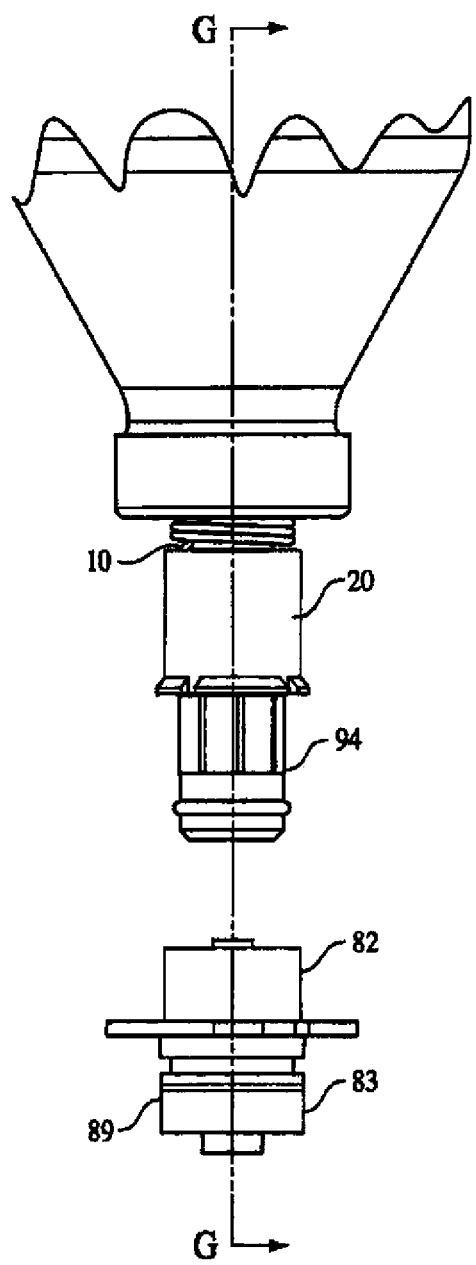
FIG. 8A is a side view of the device, reservoir, and receiving port of FIG. 7A, wherein the device is not inserted into the receiving port, and both the device and receiving port are in closed positions.
Figure 8B:
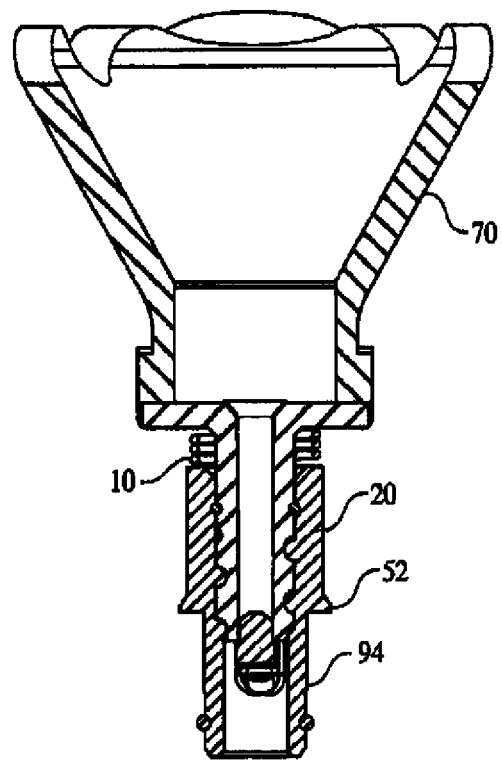
FIG. 8B is a cross-sectional view of the device, reservoir, and receiving port shown in FIG. 8A taken along G-G.
Figure 8B:
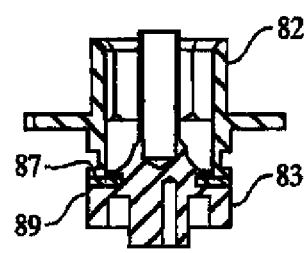
Figure 8C:
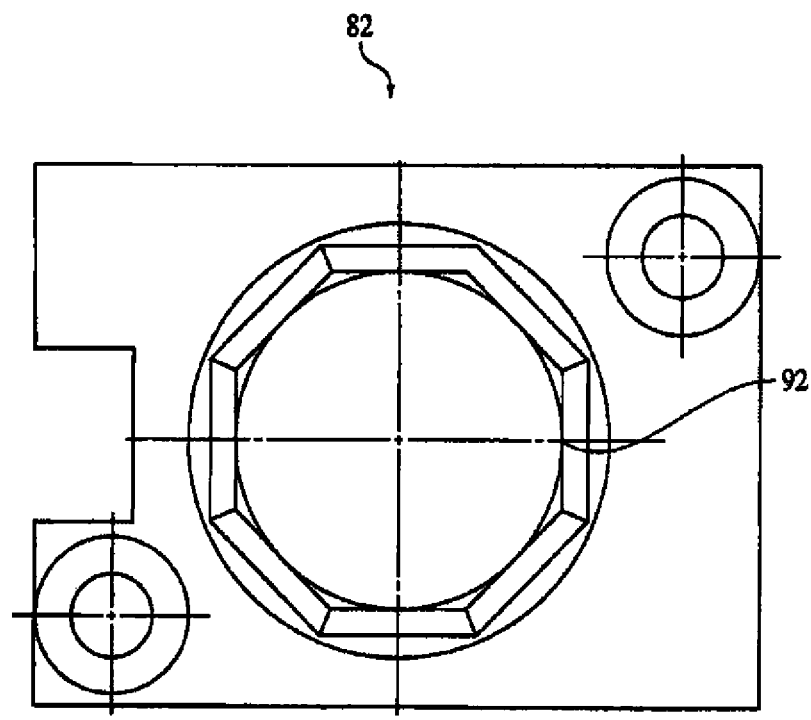
FIG. 8C is a plan view of the receiving port of FIG. 8A.

FIGS. 7A and 7B depict a non-limiting example of a device 10 in a closed position (as described above) and a receiving port 82 of a vaporizer. The receiving port 82 houses the plunger 83. In this example, the receiving port 82 is "open" because the plunger 83 does not obstruct an outlet 87 of the receiving port 82. FIGS. 8A and 8B depict the receiving port 82 in a "closed" position when the device 10 is not inserted; in this case the plunger 83 seals the outlet 87. The plunger 83 may have a gasket 89 to provide an improved seal when in the closed position. FIG. 8C illustrates one embodiment of a receiving port 82 showing an octagonal receiving surface 92 configured to mate with similarly shaped surface 94 on the second component 20 of a device 10.

Figure 7C:
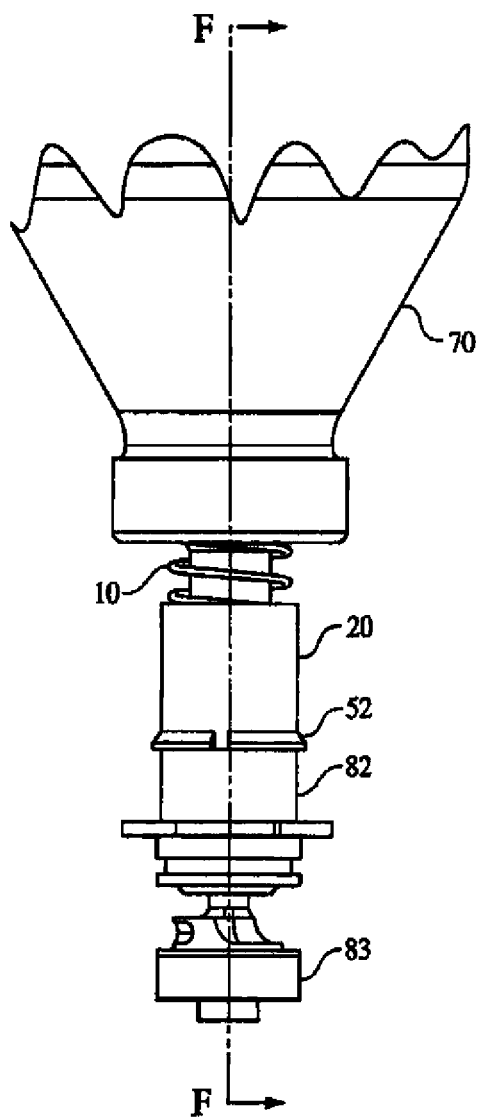
FIG. 7C is a side view of the device, reservoir, and receiving port of FIG. 7A wherein the device is in an open position and the receiving port is in an open position.
Figure 7D:
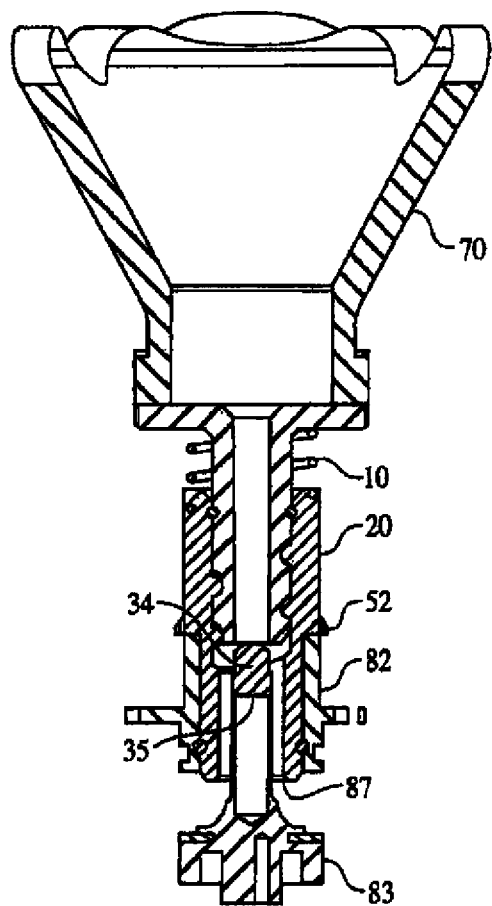
FIG. 7D is a cross-sectional view of the device, reservoir, and receiving port of FIG. 7C taken along F-F.

FIGS. 7C and 7D depict the device 10 inserted into the receiving port 82 wherein the device 10 is in an open position. In this manner, when a reservoir 70 with a device 10 is inserted into the receiving port 82 of a vaporizer, the downstream side 35 of the support member 34 depresses the plunger 83 to open the vaporizer, and in this manner makes the vaporizer ready to receive anesthetic. The reservoir 70 may then be rotated so as to open the device 10 and allow liquid anesthetic to flow into the vaporizer. In this manner, the vaporizer is made ready to receive anesthetic before anesthetic is allowed to leave the reservoir, and thus the likelihood of accidental spills is reduced.

It is to be understood that the descriptions of the invention have been simplified to illustrate characteristics that are relevant for a clear understanding of the invention. Those of ordinary skill in the art may recognize that other elements or steps are desirable or required in implementing the invention. However, because such elements or steps are well known in the art, and because they do not facilitate a better understanding of the invention, a discussion of such elements or steps is not provided herein. The disclosure herein is directed to all such variations and modifications to such elements and methods known to those skilled in the art.

It is to be understood that the invention may assume various alternative orientations and step sequences, except where expressly specified to the contrary. It is also to be understood that the specific devices and processes illustrated in the attached drawings, and described in this specification are simply exemplary embodiments of the inventive concepts defined in the appended claims. Hence, specific dimensions and other physical characteristics relating to the embodiments disclosed herein are not to be considered as limiting, unless the claims expressly state otherwise.

Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

What is claimed is:

1. An apparatus for controlling the flow of anesthetic from an anesthetic reservoir comprising:
    a first component having a base and a nozzle, the base being configured so as to be capable of being sealed and affixed to an opening of a reservoir, the nozzle being externally threaded, and wherein a through-hole extends through the base and the nozzle;
    a second component having an aperture defined by an inner surface of the second component, and wherein the aperture has internal threads for engaging with the external threads of the nozzle;
    a support member extending into the aperture from the inner surface;
    a protrusion extending from the support member toward the internal threads, wherein the protrusion is configured to be capable of sealing the through-hole in the nozzle;
    a biasing member attached to the first component and the second component, the biasing member biasing the second component relative to the first component to cause the protrusion to seal the through-hole;
    wherein a fluid in the reservoir may exit the reservoir by way of the through-hole and the aperture; and
    wherein twisting the first component and second component relative to each other causes the protrusion to seal or unseal the through-hole thereby allowing or preventing the flow of fluid.

2. The apparatus of claim 1, wherein the biasing member is a torsion spring.

3. The apparatus of claim 1, wherein the support member is orthogonal to the inner surface of the second component.

4. The apparatus of claim 1, wherein the support member intersects the inner surface of the second component at an angle of less than ninety degrees.

5. The apparatus of claim 1, further comprising a cap.

6. The apparatus of claim 1, further comprising an O-ring affixed to an exterior surface of the second component.

7. The apparatus of claim 1, wherein an exterior surface of the second component is adapted for engaging a vaporizer to prevent the second component from rotating relative to the vaporizer.

8. The apparatus of claim 1, wherein a portion of an exterior surface of the second component that mates with a vaporizer has a polygonal shape with three or more flat sides.

9. The apparatus of claim 1, wherein a downstream side of the support member is capable of depressing a plunger in order to open a vaporizer.

10. The apparatus of claim 1, wherein the base of the first component is affixed to the opening of the reservoir with a clamping ring.

11. A system comprising:
    an anesthetic reservoir; and
    an apparatus connected to the reservoir, wherein the apparatus comprises:
        a first component having a base and a nozzle, the base being configured so as to be capable of being sealed and affixed to an opening of the reservoir, the nozzle being externally threaded, and wherein a through-hole extends through the base and the nozzle;
        a second component having an aperture defined by an inner surface of the second component, and wherein the aperture has internal threads for engaging with the external threads of the nozzle;
        a support member extending into the aperture from the inner surface;
        a protrusion extending from the support member toward the internal threads, wherein the protrusion is configured to be capable of sealing the through-hole in the nozzle;
        a biasing member attached to the first component and the second component, the biasing member biasing the second component relative to the first component to cause the protrusion to seal the through-hole;
        wherein a fluid in the reservoir may exit the reservoir by way of the through-hole and the aperture; and
        wherein twisting the first component and second component relative to each other causes the protrusion to seal or unseal the through-hole thereby allowing or preventing the flow of fluid.

12. The system of claim 11, wherein the biasing member is a torsion spring.

13. The system of claim 11, wherein the support member is orthogonal to the inner surface of the second component.

14. The system of claim 11, wherein the support member intersects the inner surface of the second component at an angle of less than ninety degrees.

15. The system of claim 11, further comprising a cap.

16. The system of claim 11, further comprising an O-ring affixed to an exterior surface of the second component.

17. The system of claim 11, wherein an exterior surface of the second component is adapted for engaging a vaporizer to prevent the second component from rotating relative to the vaporizer.

18. The system of claim 11, wherein a portion of an exterior surface of the second component that mates with a vaporizer has a polygonal shape with three or more flat sides.

19. The system of claim 11, wherein a downstream side of the support member is capable of depressing a plunger in order to open a vaporizer.

20. The system of claim 11, wherein the base of the first component is affixed to the opening of the reservoir with a clamping ring.

21. A device for controlling the flow of liquid anesthetic from an anesthetic reservoir comprising:
    a first component having:
        (a) a base having a first end that is adapted to be fixedly secured to an opening of a reservoir; and (b) a nozzle extending away from the first end of the base and having at least one external thread formed thereon, wherein the nozzle and the base define a passage extending therethrough;

a second component having:
  (a) an inner surface which has at least one internal thread that is adapted to engage with the at least one external thread on the nozzle to moveably couple the second component to the first component;
  (b) an outer surface which is adapted to couple with an anesthetic device; and
  (c) an occlusion member fixedly attached to the inner surface; and a biasing member coupled to the first component and the second component to thereby bias the second component relative to the first component in a direction causing the occlusion member to seal the passage;

whereby relative rotation between the first component and second component causes the occlusion member to move between a first position in which the passage is open and a second position in which the passage is sealed by the occlusion member.

22. The device of claim 21, wherein the occlusion member comprises a cantilever support member having one end fixedly attached to the inner surface and a knob attached to a free end of the support member.

23. The device of claim 21, wherein the biasing member is a torsion spring.

24. The device of claim 21, wherein the second component has a circumferential groove formed therein and an O-ring disposed in the circumferential groove.

25. The device of claim 21, wherein a downstream side of the occlusion member is adapted to interact with a plunger of an anesthetic device.

26. The device of claim 21, wherein, in the second position, the occlusion member presses against an end of the nozzle.

27. The device of claim 21, wherein the base of the first component is affixed to the opening of the reservoir with a clamping ring.

* * * * *